(12) United States Patent
Ledden (10) Patent No.: US 11,585,808 B2
(45) Date of Patent: Feb. 21, 2023

(54) DEVICES, METHODS, AND KITS FOR MULTIPLEXING A FLUID SAMPLE VIA FLUID SAMPLE REUSE

(71) Applicant: Siemens Healthcare Diagnostics Inc., Tarrytown, NY (US)

(72) Inventor: David Ledden, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 42 days.

(21) Appl. No.: 17/174,431

(22) Filed: Feb. 12, 2021

(65) Prior Publication Data

US 2021/0164972 A1   Jun. 3, 2021

Related U.S. Application Data

(62) Division of application No. 16/310,088, filed as application No. PCT/US2017/036063 on Jun. 6, 2017, now abandoned.

(Continued)

(51) Int. Cl.
| | |
|---|---|
| *G01N 33/543* | (2006.01) |
| *G01N 33/487* | (2006.01) |
| *G01N 33/53* | (2006.01) |
| *G01N 33/541* | (2006.01) |
| *G01N 33/573* | (2006.01) |

(Continued)

(52) U.S. Cl.
CPC . *G01N 33/54366* (2013.01); *G01N 33/48714* (2013.01); *G01N 33/5308* (2013.01); *G01N 33/541* (2013.01); *G01N 33/54306* (2013.01); *G01N 33/573* (2013.01); *G01N 33/577* (2013.01); *G01N 33/68* (2013.01); *G01N 33/74* (2013.01)

(58) Field of Classification Search
CPC ............. G01N 33/00; G01N 33/54366; G01N 33/48714; G01N 33/5308; G01N 33/541; G01N 33/54306; G01N 33/573; G01N 33/577; G01N 33/68; G01N 33/74; G01N 35/10; G01N 35/00; G01N 2035/00; G01N 1/00; B01L 3/02; B01L 3/00
See application file for complete search history.

(56) References Cited

U.S. PATENT DOCUMENTS

| | | |
|---|---|---|
| 5,356,785 A | 10/1994 | McMahon et al. |
| 9,250,229 B2 | 2/2016 | Holmes |

(Continued)

FOREIGN PATENT DOCUMENTS

| | | |
|---|---|---|
| JP | H055737 A | 1/1993 |
| JP | H0824674 A | 1/1996 |

(Continued)

OTHER PUBLICATIONS

Miller et al., "Comparision of novel pro-BNP 1-108 and standard BNP assays in heart failure patients", Year: 2012, Clinica Chimica Acta, vol. 413, pp. 920-926.

(Continued)

*Primary Examiner* — Melanie Brown
*Assistant Examiner* — Jennifer H. Tieu (57) ABSTRACT

Devices, methods, and kits for detecting at least two analytes present within a small volume single fluid sample obtained from patient for the creation of a multiplexed panel of the various analytes present within the single fluid sample are disclosed.

20 Claims, 7 Drawing Sheets

Related U.S. Application Data (60) Provisional application No. 62/351,530, filed on Jun. 17, 2016.

(51) Int. Cl.
  *G01N 33/577* (2006.01)
  *G01N 33/68* (2006.01)
  *G01N 33/74* (2006.01)

(56) References Cited

U.S. PATENT DOCUMENTS

| | | |
|---|---|---|
| 2002/0164807 A1 | 11/2002 | Itaya et al. |
| 2003/0007897 A1 | 1/2003 | Creasey |
| 2005/0019950 A1* | 1/2005 | Gierde .................. B01J 20/285 |
| | | 436/180 |
| 2007/0154895 A1 | 7/2007 | Spaid et al. |
| 2008/0156118 A1 | 7/2008 | Takaya et al. |
| 2009/0088336 A1 | 4/2009 | Burd et al. |
| 2012/0046203 A1 | 2/2012 | Walsh et al. |
| 2012/0052560 A1 | 3/2012 | Knight et al. |
| 2013/0078625 A1 | 3/2013 | Holmes et al. |
| 2014/0274901 A1 | 9/2014 | Ichiki et al. |

FOREIGN PATENT DOCUMENTS

| | | |
|---|---|---|
| JP | 2008164456 A | 7/2008 |
| WO | 9836278 A1 | 8/1998 |
| WO | 9936564 A1 | 7/1999 |
| WO | 02082051 A2 | 10/2002 |
| WO | 2012129611 A1 | 10/2012 |

OTHER PUBLICATIONS

Hawkridge et al., "Quantitative mass spectral evidence for the absence of circulating brain natriuretic peptide (BNP-32) in severe human heart failure", Year: Nov. 29, 2005, PNAS, vol. 102, No. 48, pp. 17442-17447.

International Search Report and Written Opinion of International Application No. PCT/US2017/036063 dated Aug. 22, 2017.

European Search Report and Written Opinion of European Application No. 17813794.9 dated Feb. 19, 2019.

Extended European Search Report and Written Opinion of European Application No. 17813794.9 dated May 28, 2019.

Petrou, et al.; "Multi-Analyte Capillary Immunosensor for the Determination of Hormones in Human Serum Samples,"; Biosensors and Bioelectronics; Apr. 30, 2002 (Apr. 30, 2002). vol. 17; pp. 261-268.

Nedelkov, et al.; "High-Throughput Comprehensive Analysis of Human Plasma Proteins: A Step Toward Population Proteomics," Mar. 15, 2004; Analytical Chemistry vol. 76 No. 6, pp. 1733-1737.

Hydow Park, New Technique for Solid-Phase Immunoassay: Application to Hepatitis B Surface Antigen, 1979, Clin. Chem. vol. 25 No. 1, pp. 178-182.

BioMerieux Inc. VIDAS(R) Toxo IgG Avididty Assy 510(k) Substantial Equivalence Determination Decision Summary, Assay Only Template; Internet Archive Wayback Machine capture on Feb. 25, 2017, pp. 1-16.

Niederkofler et al.,"Novel mass spectrometric immunoassays for the rapid structural characterization of plasma apolipoproteins", 2003, Journal of Lipid Research, vol. 44, pp. 630-639.

Li et al., "Handbook of LC-MS Bioanalysis: Best Practices, Experimental Protocols, and Regulations", Dec. 31, 2013, John Wiley & Sons, Inc., p. 539.

Niederkofler et al.,"Detection of Endogenous B Type Natriuretic Peptide at Very Low Concentrations in Patients With Heart Failure", Nov. 2008, DOI: 10.1161/CIRCHEARTFAILURE.108.790774, pp. 258-264.

Whiteaker et al., "Sequential Multiplexed Analyte Quantification Using Peptide Immunoaffinity Enrichment Coupled to Mass Spectrometry", Dec. 27, 2011, MCP Papers in Press, Molecular & Cellular Proteomics 11.6, pp. 1-10.

* cited by examiner

DEVICES, METHODS, AND KITS FOR MULTIPLEXING A FLUID SAMPLE VIA FLUID SAMPLE REUSE

CROSS REFERENCE TO RELATED APPLICATIONS

This application is a divisional of U.S. Ser. No. 16/310,088, filed Dec. 14, 2018; which is a U.S. national stage application filed under 35 USC § 371 of International Application No. PCT/US2017/036063, filed Jun. 6, 2017; which claims priority to U.S. Provisional Application 62/351,530, filed Jun. 17, 2016. The entire contents of the above-referenced patent applications are hereby expressly incorporated herein by reference.

STATEMENT REGARDING FEDERALLY FUNDED RESEARCH OR DEVELOPMENT

Not Applicable.

TECHNICAL FIELD

The presently disclosed and claimed inventive concept(s) relate to a device(s) and method(s) for the detection of at least two analytes, said analytes being of different and distinct compositions, present within a small volume of a single fluid sample. As a result of such detection, a multiplexed panel of the various analytes present within the small volume of the single fluid sample is achieved, while mitigating single fluid sample loss/reduction and allowing for re-use of the single fluid sample.

BACKGROUND

Numerous devices and methods exist for detecting analytes that may be present in a fluid sample. However, the currently employed devices and methods require the use of multiple fluid samples and/or aliquots of a single fluid sample for the detection of analytes present in such sample(s). Such devices and methods require a large volume of the fluid sample, the collection of multiple fluid samples from a patient in order to achieve analyte detection, and/or result in fluid sample loss/reduction due to multiple aliquots being taken from the fluid sample for analyte detection. Accordingly, a need exists for new and improved devices and methods of high sensitivity that allow a small volume of a single fluid sample obtained from a patient to be re-used in order to detect at least two analytes present in the single fluid sample. Such devices and methods thereby allow for the creation of a multiplexed panel associated with the various analytes present in the single fluid sample. It is to such devices and methods, as well as kits related thereto, that the presently disclosed and claimed inventive concept(s) is directed.

DETAILED DESCRIPTION

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "purified" as used herein means at least one order of magnitude of purification is achieved compared to the starting material or of material in its natural state, for example but not by way of limitation, two, three, four or five orders of magnitude of purification of the starting material or of the natural material. Thus, the term "purified" as utilized herein does not necessarily mean that the material is 100% purified, and therefore such term does not exclude the presence of other material(s) present in the purified composition.

The term "sample" as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperotineal fluid, cystic fluid, sweat, interstitial fluid, tears, mucus, urine, bladder wash, semen, combinations, and the like. The volume of the sample utilized in accordance with the presently disclosed and claimed inventive concept(s) is from about 1 to about 100 microliters. As used herein, the term "small volume" as it relates to the sample utilized in accordance with the presently disclosed and claimed inventive concept(s) means from about 0.1 microliter to about 90 microliters, or from about 1 microliter to about 75 microliters, or from about 2 microliters to about 60 microliters, or less than or equal to about 50 microliters.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

Turning now to particular embodiments of the presently claimed and disclosed inventive concept(s), devices, methods, and kits are herein disclosed of high sensitivity that allow for a small volume of a single fluid sample obtained from a patient to be re-used in order to detect at least two analytes present in the single fluid sample.

The kit can further include a set of written or pictorial instructions (or information on how to obtain instructions, either written or pictorial, from the internet) explaining how to use the kit. A kit of this nature can be used in any of the methods described or otherwise contemplated herein.

It is contemplated that virtually any reagent used in the fields of biological, chemical, or biochemical analyses could be used in the devices, kits, and methods of the presently claimed and disclosed inventive concept(s). It is contemplated that these reagents may undergo physical and/or chemical changes when bound to an analyte of interest whereby the intensity, nature, frequency, or type of signal generated by the reagent-analyte complex is proportional to the concentration of the analyte existing within the fluid sample. These reagents may contain indicator dyes, metal, enzymes, polymers, antibodies, and electrochemically reactive ingredients.

Any method of detecting and measuring the analyte in a fluid sample can be used in the devices, kits, and methods of the presently claimed and inventive concepts. A variety of assays for detecting analytes are well known in the art and include, but are not limited to, enzyme inhibition assays, antibody stains, latex agglutination, and immunoassays, such as, radioimmunoassays. The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG1, IgG2, IgG3, IgG4, IgA1, and IgA2).

The term "binding partner" as used herein will be understood to refer to any molecule capable of associating with another molecule. For example, but not by way of limitation, the binding partner may be an antibody (including polyclonal or monoclonal antibodies), antibody fragments (such as, but not limited to, Fab, Fab', F(ab')2, Fv, scFv, Fd, diabodies, single-chain antibodies, and other antibody fragments that retain at least a portion of the variable region of the intact antibody), a receptor, a ligand, aptamers, antibody substitute proteins or peptides (i.e., engineered binding proteins/peptides), molecular imprinted polymers (i.e., inorganic matrices), combinations or derivatives thereof, as well as any other molecules capable of binding to the analyte(s).

The term "non-reacted portion" as used herein will be understood to refer to any portion of the single fluid sample in which an analyte has not become associated with an immobilized capture antibody/binding partner present on an inner surface of a pipette and which is re-dispensed into the sample receptacle. The term "reacted portion" as used herein will be understood to refer to any portion of the single fluid sample in which an analyte has become associated with an immobilized capture antibody/binding partner on an inner surface of a pipette and which is not re-dispensed into the sample receptacle.

While immunoassays are primarily discussed herein, a person having ordinary skill in the art should readily understand that the presently disclosed and claimed inventive concept(s) are not strictly limited to immunoassays and may include, by way of example and not by limitation, nucleic acid capture assays and serology-based assays. Immunoassays, including radioimmunoassays and enzyme-linked immunoassays, are useful methods for use with the presently claimed and disclosed inventive concepts. A variety of immunoassay formats, including, for example, competitive and non-competitive immunoassay formats, antigen/analyte capture assays and two-antibody sandwich assays can be used in the methods of the invention. Enzyme-linked immunosorbent assays (ELISAs) can be used in the presently claimed and disclosed inventive concepts, as well. In the case of an enzyme immunoassay, an enzyme is typically conjugated to a second antibody, generally by means of glutaraldehyde, periodate, hetero-bifunctional crosslinking agents, or biotin-streptavidin complexes. As will be readily recognized, however, a wide variety of different conjugation techniques exist which are readily available for use with the presently disclosed and claimed inventive concept(s) to one skilled in the art.

In certain embodiments, the analytes are detected and measured using chemiluminescent detection. For example, in certain embodiments, analyte-specific capture antibodies are used to capture an analyte present in the biological fluid sample. The analyte-specific capture antibodies (and/or the specific analyte(s)) may be labeled with a chemiluminescent detection antibody to thereby detect if an analyte is present in the biological fluid sample. Any chemiluminescent label and detection system can be used in the present devices and methods. Chemiluminescent detection antibodies/binding partners can be obtained commercially from various sources. Methods of detecting chemiluminescent detection antibodies/binding partners are known in the art and are not further discussed here in detail.

Fluorescent detection also can be useful for detecting analytes in the presently claimed and disclosed inventive concepts. Useful fluorochromes include, but are not limited to, DAPI, fluorescein, lanthanide metals, Hoechst 33258, R-phycocuanin, B-phycoerythrin, R-phycoerythrin, rhodamine, Texas red and lissamine. Fluorescent compounds can be chemically coupled to antibodies/binding partners without altering their binding capacity. When activated by illumination with light of a particular wavelength, the fluorochrome-labeled antibody/binding partner absorbs the light energy, inducing a state of excitability in the molecule, followed by emission of the light as a characteristic color that is visually detectable. Radioimmunoassays (RIAs) can also be useful in certain methods of the invention. Such assays are well known in the art. Radioimmunoassays can be performed, for example, with $^{125}$I-labeled detection antibodies/binding partners that are associated with either the analyte being detected and/or the immobilized capture antibodies/binding partners.

Assays, including, but not limited to, immunoassays, nucleic acid capture assays, and serology-based assays, can be developed for a multiplexed panel of proteins, peptides, and nucleic acids which may be contained within a fluid sample, with such proteins and peptides including, for example but not by way of limitation, albumin, hemoglobin, myoglobin, α-1-microglobin, immunoglobins, enzymes, glycoproteins, protease inhibitors, drugs, and cytokines. The device may be used for the analysis of any fluid sample, including, without limitation, whole blood, plasma, serum, or urine. Table 1 below, by way of example only and not by way of limitation, illustrates particular analytes of interest as well as respective antibodies/binding partners which may be used in the presently disclosed and claimed inventive concept(s).

TABLE 1

Non-Limiting Examples of Analytes
and Antibodies/Binding Partners 25-hydroxyvitamin D; 1,25 dihydroxyvitamin D - serum/plasma
Acetaminophen - serum/plasma
ACTH - serum/plasma
AFP - serum
ALB - serum/plasma
Alpha-1-Antitrypsin blood SERPINA 1
Alpha-1-Antitrypsin serum/plasma
Alpha-1-Acid Glycoprotein serum/plasma
Amphetamines - urine
Amylase - pancreatitis blood, urine or peritoneal sample
ANA - autoimmune (SLE) serum/plasma
Androstenedione serum/plasma
Anti-double-stranded DNA, IgG -serum
Apolipoprotein A-I - serum/plasma
Barbituates - urine
Benzodazepines - serum/plasma
Benzodazepines - urine
Beta2 Microglobulin - serum or 24 h urine
Blood Typing (Immunoassay) - Panel/Whole Blood
BNP - plasma
Borrelia burgdorferi Antibodies (Lyme Disease) - serum/plasma
CA -125 - serum/plasma
CA 15-3 - serum/plasma
CA 19-9 - serum/plasma
CA 27.29 - serum/plasma
Calcitonin - serum/plasma
Carbamazepine - serum/plasma

TABLE 1-continued

Non-Limiting Examples of Analytes and Antibodies/Binding Partners

Cardiac-specific Troponin I and Troponin T - serum/plasma
Cardiolipin Antibodies (IgG) - serum/plasma
CEA - serum/plasma
Celiac Panel (4 plex) - serum/plasma
Chlamydia trachomatis DNA Qualitative
Chlamydia trachomatis DNA Qualitative - Swab Collection
Chlamydia Trachomatis, DNA, Qualitative/Gonorrhea, DNA, Qualitative
Cholinesterase - serum/plasma
CKMB - serum/plasma
CMV Antibody IgG - serum/plasma
CMV Antibody IgM - serum/plasma
Cocaine - urine
Collagen Crosslinks - serum/plasma
Cortisol, Total - serum/plasma
C-peptide (insulin) - serum/plasma
CRP -serum/plasma
Cyclic Citrullinated Peptide (CCP) Antibody, IgG - serum/plasma
Cyclosporine, A (immunosupressant) - serum/plasma
Cystatin C (kidney) - serum/plasma
D-Dimer -serum/plasma
Deaminated Gliadin Peptide IgA -serum/plasma
Deaminated Gliadin Peptide IgG -serum/plasma
Dehydroepiandrosterone Sulfate - serum/plasma
Dehydroepiandrosterone Sulfate - serum/plasma GC/MS
Digoxin - serum/plasma TDM
Dolphine (Methadone)
Double Stranded DNA (*Crithidia luciliae*) Antibody, IgG
*E. coli* Shiga Toxin
EBV Antibody (NA IgG) - serum
EBV Antibody Panel (NA IgG; VCA IgG; VCA IgM) - serum
EBV Antibody Panel (VCA IgG) - serum
EBV Antibody Panel (VCA IgM) - serum
Ecstasy (MDMA)
Endomysial Antibody; EMA IgA - serum (ELISA and IFA)
Endomysial Antibody; EMA IgG - serum (ELISA and IFA)
Estradiol - serum
Estriol - serum/plasma
Estriol - urine (24 hour collection)
Ferritin - serum
Fibrinogen - plasma
Folate - serum
Follicle Stimulating Hormone - serum/plasma
Follicle Stimulating Hormone - urine
Gastrin - serum
Gentamicin - serum
Growth Hormone - serum
H. pylori, IgG - serum
Haptoglobin, Quantitative - serum
hCG - serum/plasma
hCG - urine
Hepatitis A Antibody (HAAb), Total - serum
Hepatitis A, IgM - serum
Hepatitis B Core Antibody, IgM - serum
Hepatitis B Core Antibody, Total - serum
Hepatitis B Surface Antibody, Total - serum
Hepatitis B, DNA, Quantitative
Hepatitis C Antibody - serum
Hepatitis C Genotyping
HER2/neu, Quantitative - serum
Herpes Simplex Virus, Type 1, IgG - serum
HIV-1/2 Ab - serum
Homocysteine - serum/plasma
hsCRP - serum/plasma
Human Immunodeficiency Virus 1, RNA Viral Load, Quantitative
Human Immunodeficiency Virus Antibody Test - serum
IgA, serum
IgE
IgG, serum
IgM, serum
Insulin - serum/plasma
Lactate Dehydrogenase, Total and Isoenzymes - Body Fluid/Serum
Lipase - serum
Luteinizing Hormone - serum
Luteinizing Hormone - urine
Measles (Rubeola Antibody), IgG - serum/CSF
Methadone Metabolite - urine
Microalbumin - urine
Mumps Antibody, IgG - serum
Myoglobin - serum/plasma
Neisseria gonorrhoeae, DNA, Qualitative
Nuclear Antigen Antibody, Jo-1 - serum
Nuclear Antigen Antibody, RNP - serum
Nuclear Antigen Antibody, Scl-70 - serum
Nuclear Antigen Antibody, Sm - serum
Nuclear Antigen Antibody, SSA - serum
Nuclear Antigen Antibody, SSB - serum
Opiates - urine
Parathyroid Hormone - serum
Phencyclidine (PCP) - urine
Phenobarbital - serum/plasma
Phenytoin, Total - serum/plasma
Progesterone - serum
Prolactin - serum
Propoxyphene
PSA, Free - serum/plasma
PSA, Total - serum
RBC Antibody ID (Immunoassay) - Whole Blood
Rheumatoid Factor, Total - serum
Rubella Antibodies, IgG - serum
Rubella Antibodies, IgM - serum
Salicylate
Sex Hormone-binding Globulin (SHBG)
Sex Hormone-binding Globulin (SHBG) - serum/plasma
Streptolysin O Antibody, Titer (ASO) - serum
Syphilis Screen (Treponema Pallidum Antibody) - serum
T3, Free - Triiodothyronine, Free - serum
T3, Total - Triiodothyronine, Total - serum
T4, Free - Thyroxine, Free - serum
T4, Total - Thyroxine, Total - serum
Testosterone, Free - serum/plasma
Testosterone, Total - serum/plasma
THC - urine
Theophylline - serum
Thyroglobulin - serum or plasma
Thyroglobulin Antibodies - serum
Thyroid Peroxidase Antibody (TPO)
Thyroid Stimulating Hormone (TSH) - serum
Thyroxine Binding Globulin - serum
Tobramycin -serum/plasma
Toxoplasma, IgG - serum
Toxoplasma, IgM - serum
Tricyclic Antidepressants - urine
Tricyclic Antidepressants, Blood
Triiodothyronine Uptake (T3 Uptake) - serum
Valproic Acid - serum/plasma
Vancomycin - serum
Varicella-Zoster Antibody - serum
Viral Hepatitis C, RNA, Quantitative
Vitamin B12 - serum In addition and as illustrated in Table 1 above, while the Figures specifically show immobilized capture antibodies present on the inner surface(s) of the pipette(s), it should be readily understood by a person having ordinary skill in the art that any binding partner may be immobilized on the inner surface(s) of the pipette(s) to accomplish the inventive concept(s), including, by way of example and not by limitation, nucleic acids and fragments thereof, antigens, ligands, and any binding partner capable of accomplishing the presently disclosed and claimed inventive concept(s).

Figure 1A:
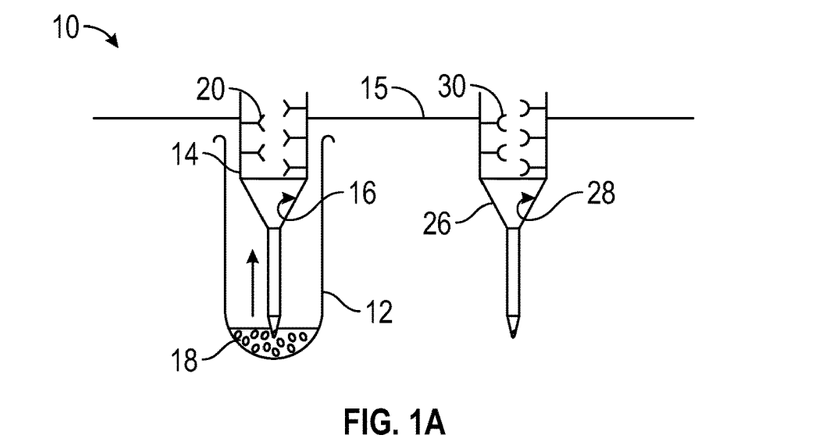
FIGS. 1A, 1B, and 1C are detailed perspective views of one embodiment of a device constructed in accordance with the presently disclosed and claimed inventive concept(s) and use thereof in a method as described herein.
Figure 1B:
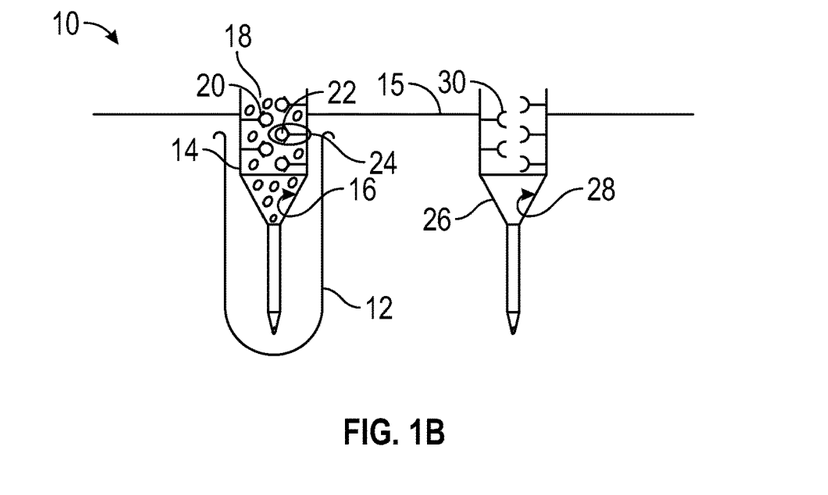
Figure 1C:
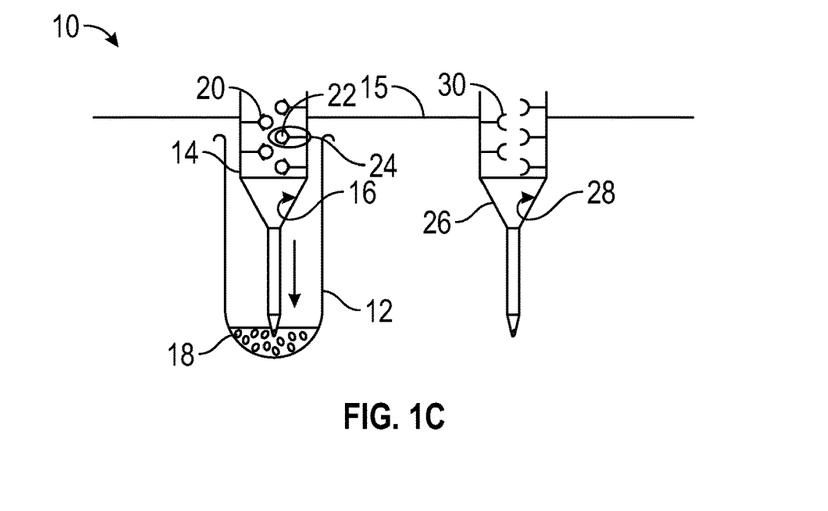

Referring now to the drawings, and more particularly to FIGS. 1A-1C, shown therein is an exemplary embodiment of a device 10 that detects the presence and/or absence of at least two analytes in a single fluid sample obtained from a patient. The device 10 comprises a sample receptacle 12 and at least one pipette 14, i.e., the device 10 may contain 1, 2, 5, 10, 15, 20, 50, 100, 100 or 1000 pipettes attached to one another via a mechanical connecting web or a pipetting station, such as pipetting station 15 for example, but not by way of limitation. By way of example only, FIGS. 1A-1C depict two pipettes shown as 14 and 26 to illustrate that the device 10 may comprise more than one pipette. For purposes of clarity only and not by way of limitation, the device 10 shown in FIGS. 1A-1C shall be described with reference only to pipette 14. Pipette 14 comprises an inner surface 16 on which at least one immobilized capture antibody 20 is present. The sample receptacle 12 contains a single fluid sample 18 that has been obtained from a patient. As shown in FIG. 1A with respect to pipette 14, five immobilized capture antibodies 20 are shown as being immobilized on the inner surface 16. However, one of ordinary skill in the art would recognize that any number of immobilized capture antibodies 20 may be immobilized on the inner surface 16 of the pipette 14.

As depicted in FIG. 1B, at least a portion of the single fluid sample 18 has been withdrawn into the pipette 14 such that the single fluid sample 18 is in contact with the inner surface 16 of the pipette 14. As a result of this contact, the single fluid sample 18 comes into contact with immobilized capture antibody/binding partner 20. If an analyte of interest is present in the single fluid sample 18, at least one analyte-antibody/binding partner complex 24 is formed by an association between the analyte 22 present in the single fluid sample 18 and the at least one immobilized capture antibody/binding partner 20 present on the inner surface 16 of the pipette 14.

As shown in FIG. 1C, a non-reacted portion of the single fluid sample 18 is re-dispensed into the sample receptacle 12 from the pipette 14. The analyte 22, if present, remains within the pipette 14 (a reacted portion of the single fluid sample 18) due to the association between the analyte 22 and the immobilized capture antibody 20 forming the first analyte-antibody/binding partner complex 24 present on the inner surface 16 of the pipette 14. Detection of the analyte 22 within the pipette 14 can be accomplished in accordance with any of the methodologies described herein or well known in the art. The detection can be either a qualitative or quantitative assessment of the presence of analyte 22 within the pipette 14 and thereby indicates the presence of analyte 22 in the single fluid sample 18.

Thereafter, pipette 14 is removed from the sample receptacle 12 and pipette 26 is placed within the sample receptacle 12. Thereafter, at least a portion of the non-reacted portion of the single fluid sample 18 is withdrawn into pipette 26 and into contact with an inner surface 28 of pipette 26 to which a second immobilized capture antibody 30 is bound. A second analyte (not shown) which is different in composition than the analyte 22 is thereafter, if present in the single fluid sample 18, bound to the second immobilized capture antibody/binding partner 30 bound to inner surface 28 of pipette thereby forming a second analyte-antibody/binding partner complex (not shown).

Referring now to FIGS. 2A-2L, shown therein is an alternate embodiment of a device 10A that detects the presence and/or absence of at least two analytes in a single fluid sample obtained from a patient. The device 10A comprises a sample receptacle 12A, a first pipette 14A, a second pipette 26A, and a third pipette 36A. While the non-limiting embodiment of device 10A as shown in FIGS. 2A-2L is shown as comprising three pipettes, three analytes, and three distinct and different immobilized capture antibodies/binding partners, it should be understood to a person having ordinary skill in the art that device 10A can be comprised of any number of pipettes, analytes, and different and distinct immobilized capture antibodies/binding partners in order to detect the presence of at least two analytes present within a single fluid sample obtained from a patient. For example, the device 10A may contain 1, 2, 5, 10, 15, 20, 50, 100, or 1000 pipettes. The pipettes may be attached to one another via a mechanical connecting web or pipetting station, such as pipetting station 15A for example, but not by way of limitation. In addition, the process of sequentially disposing the first pipette 14A, the second pipette 26A, and the third pipette 36A within the sample receptacle 12A can be accomplished either by a manual or automated process(es) via use of the pipetting station 15A.

As shown in FIGS. 2A-2D, the first pipette 14A comprises an inner surface 16A on which a first immobilized capture antibody 20A is present. As shown in FIGS. 2A-2D, five first immobilized capture antibodies/binding partners 20A are shown as being immobilized on the inner surface 16A. However, one of ordinary skill in the art would recognize that any number of first immobilized capture antibodies/binding partners 20A may be immobilized on the inner surface 16A of the first pipette 14A. The first pipette 14A is disposed within sample receptacle 12A which contains a single fluid sample 18A obtained from a patient, said single fluid sample 18A comprising at least two analytes. At least a portion of the single fluid sample 18A is withdrawn into the first pipette 14A such that the single fluid sample 18A is in contact with the inner surface 16A of the first pipette 14A. As a result of this contact, the single fluid sample 18A comes into contact with the first immobilized capture antibody/binding partner 20A. If a first analyte of interest is present in the single fluid sample 18A, at least one first analyte-antibody/binding partner complex 24A is formed by an association between the first analyte 22A present in the single fluid sample 18A and the first immobilized capture antibody 20A present on the inner surface 16A of the first pipette 14A. A non-reacted portion of the single fluid sample 18A is re-dispensed into the sample receptacle 12A from the first pipette 14A. The first analyte 22A, if present, remains within the first pipette 14A (a reacted portion of the single fluid sample 18A) due to the association between the first analyte 22A and the first immobilized capture antibody/binding partner 20A forming the first analyte-antibody complex 24A present on the inner surface 16A of the first pipette 14A. Detection of the first analyte 22A within the first pipette 14A can be accomplished in accordance with any of the methodologies described herein or well known in the art. The detection can be either a qualitative or quantitative assessment of the presence of the first analyte 22A within the pipette 14A and thereby indicative of the presence of the first analyte 22A in the single fluid sample 18A. After the non-reacted portion of the single fluid sample 18A is re-dispensed into the sample receptacle 12A from the first pipette 14A, the second pipette 26A is transitioned so that is capable of being disposed within the sample receptacle 12A.

Referring now to FIGS. 2E-2H, the second pipette 26A comprises an inner surface 28A on which a second immobilized capture antibody/binding partner 30A is present. The second immobilized capture antibody/binding partner 30A is different in analyte specificity from the first immobilized capture antibody/binding partner 20A, thereby allowing for association with and detection of a different and distinct analyte present in the single fluid sample 18A from the first analyte 22A present in the single fluid sample 18A. The second pipette 26A is disposable within sample receptacle 12A which contains the non-reacted portion of the single fluid sample 18A which has been re-dispensed into the sample receptacle 12A from the first pipette 14A. As shown in FIGS. 2E-2H, with respect to the second pipette 26A, five second immobilized capture antibodies/binding partners 30A are shown as being immobilized in the inner surface 28A. However, one of ordinary skill in the art would recognize that any number of second immobilized capture antibodies/binding partners 30A may be immobilized on the inner surface 28A of the second pipette 26A. At least a portion of the non-reacted portion of the single fluid sample 18A is withdrawn into the second pipette 26A such that the single fluid sample 18A is in contact with the inner surface 28A of the second pipette 26A. As a result of this contact, the single fluid sample 18A comes into contact with the second immobilized capture antibody/binding partner 30A. If a second analyte of interest is present in the single fluid sample 18A, at least one second analyte-antibody/binding partner complex 34A is formed by an association between the second analyte 32A present in the single fluid sample 18A and the second immobilized capture antibody/binding 30A present on the inner surface 28A of the second pipette 26A. A non-reacted portion of the single fluid sample 18A is re-dispensed into the sample receptacle 12A from the second pipette 26A. The second analyte 32A, if present, remains within the second pipette 26A (a reacted portion of the single fluid sample 18A) due to the association between the second analyte 32A and the second immobilized capture antibody/binding partner 30A forming the second analyte-antibody/binding partner complex 34A present on the inner surface 28A of the second pipette 26A. Detection of the second analyte 32A within the second pipette 26A can be accomplished in accordance with any of the methodologies described herein or well known in the art. The detection can be either a qualitative or quantitative assessment of the presence of the second analyte 32A within the second pipette 26A and thereby indicative of the presence of the second analyte 32A in the single fluid sample 18A=. After the non-reacted portion of the single fluid sample 18A is re-dispensed into the sample receptacle 12A, the third pipette 36A is transitioned so that it is capable of being disposed within the sample receptacle 12A.

Figure 2A:
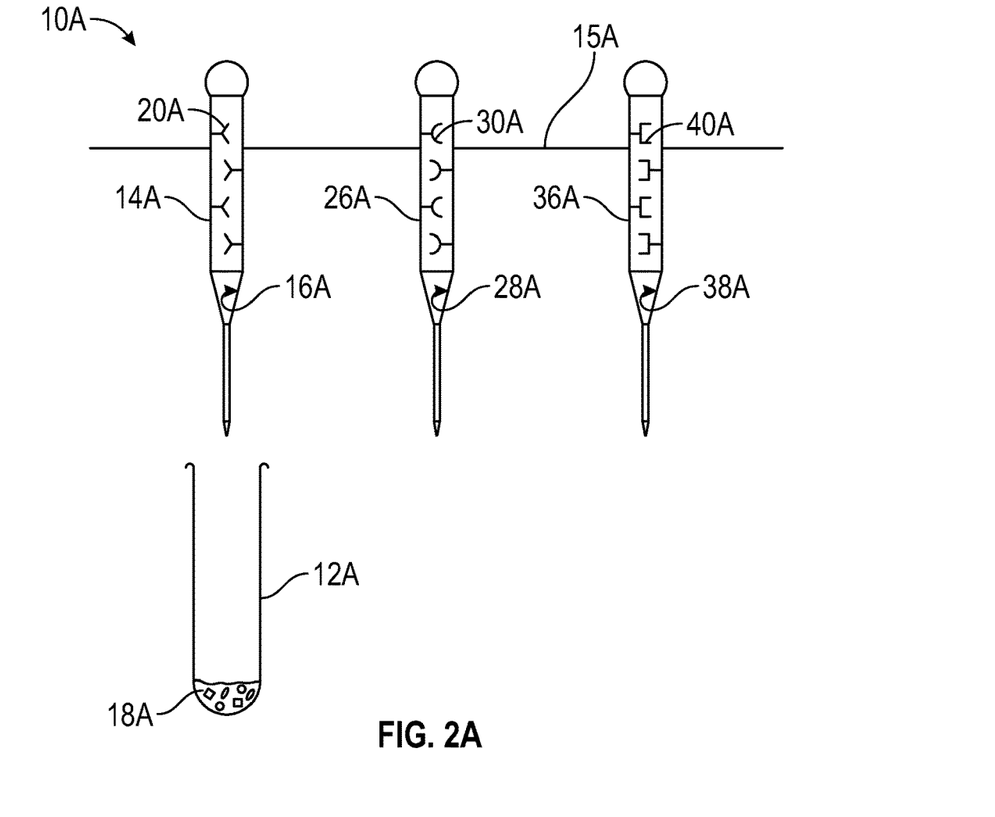
FIGS. 2A-2L are perspective views of an alternate embodiment of a device of the presently disclosed and claimed inventive concept(s) and use thereof in a method as described herein.
Figure 2B:
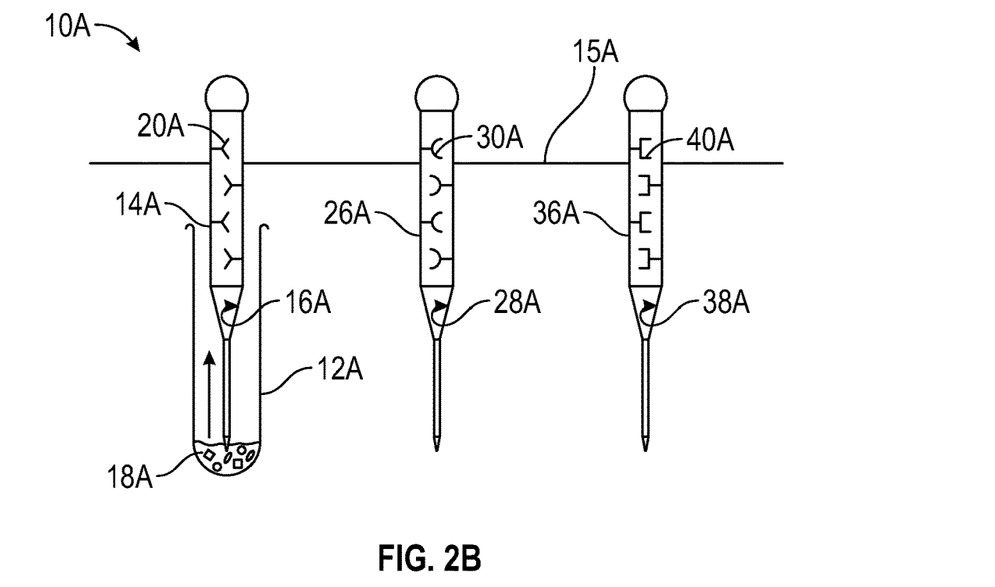
Figure 2C:
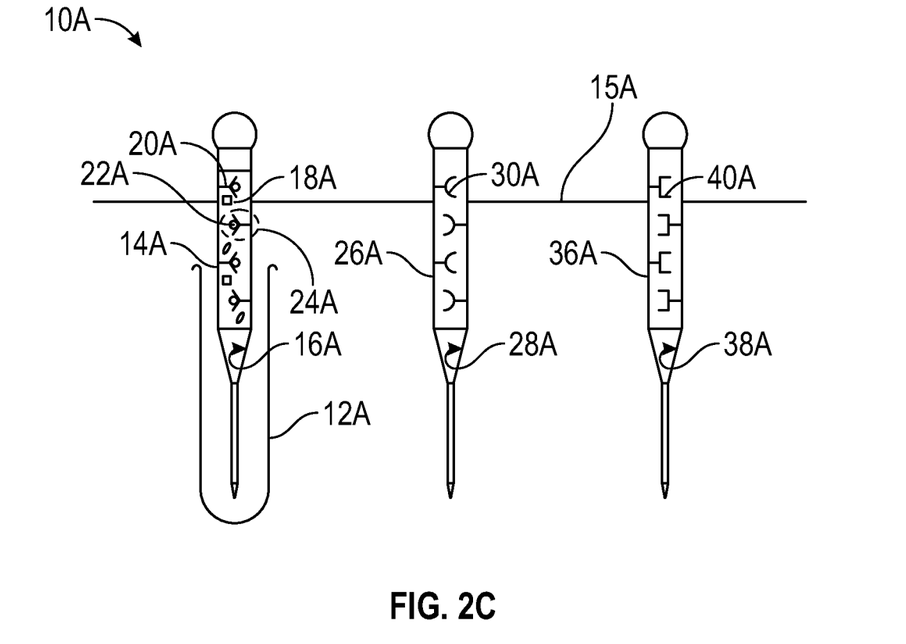
Figure 2D:
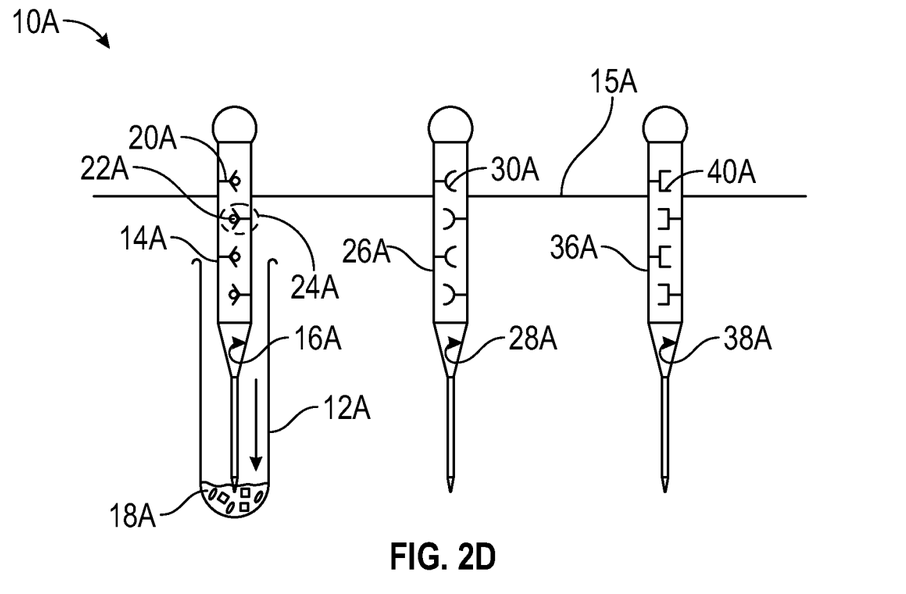
Figure 2E:
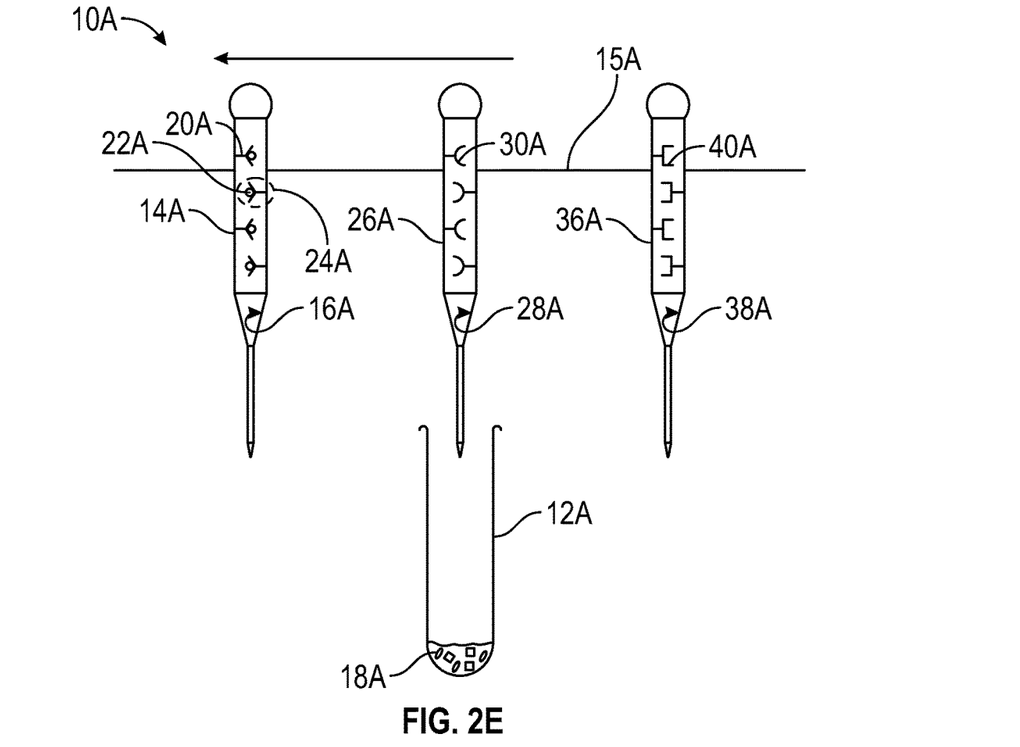
Figure 2F:
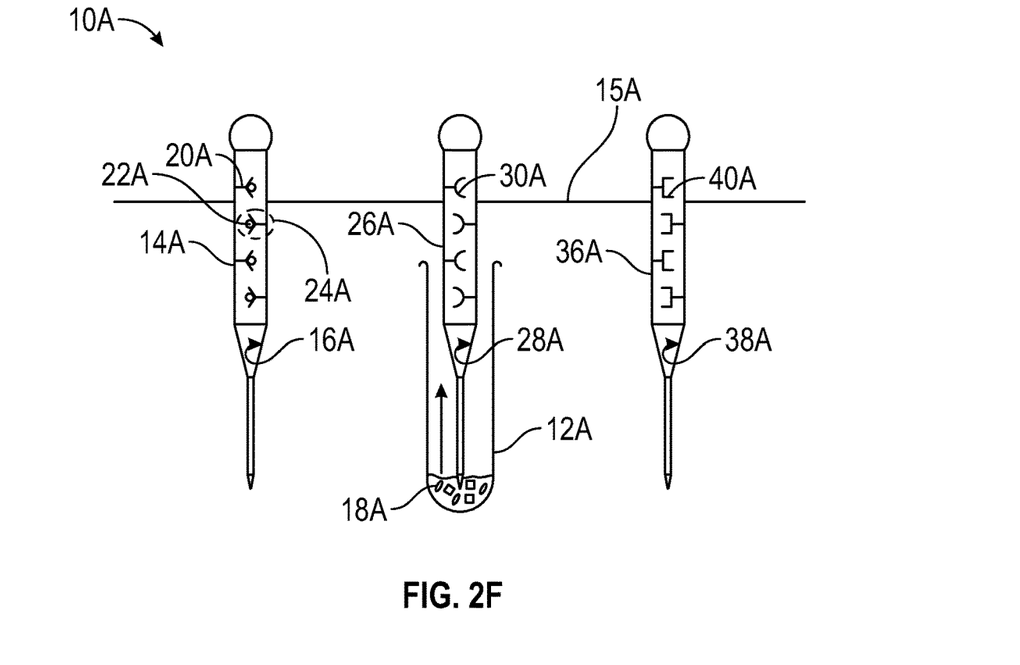
Figure 2G:
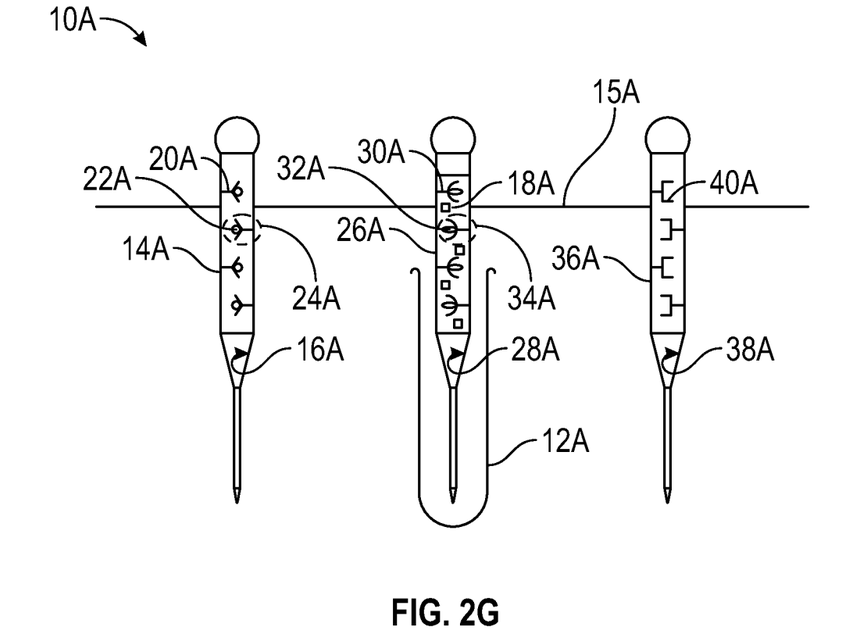
Figure 2H:
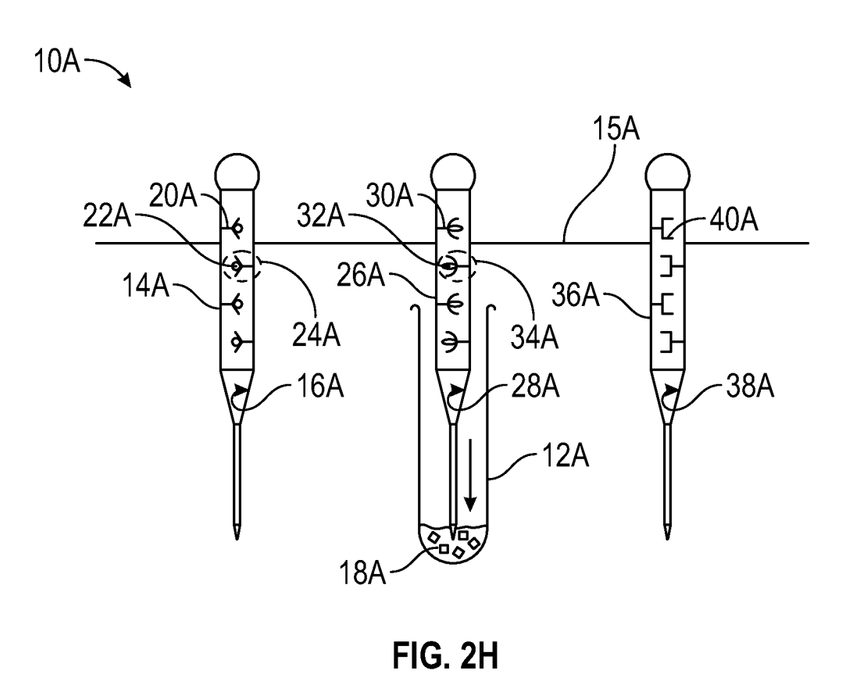
Figure 2I:
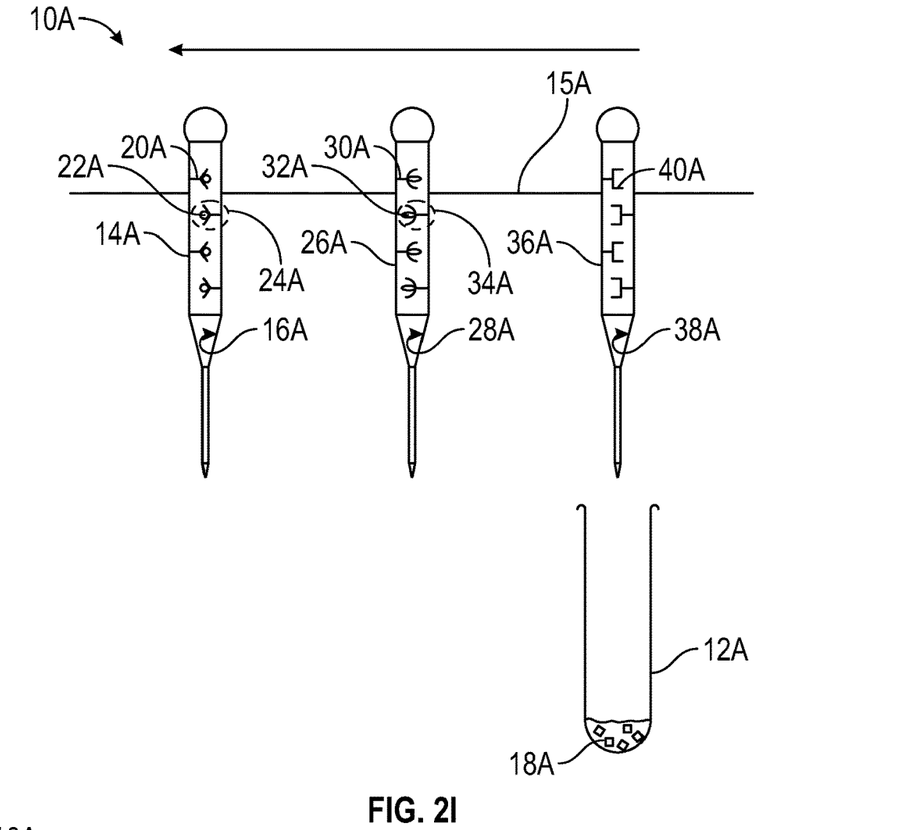
Figure 2J:
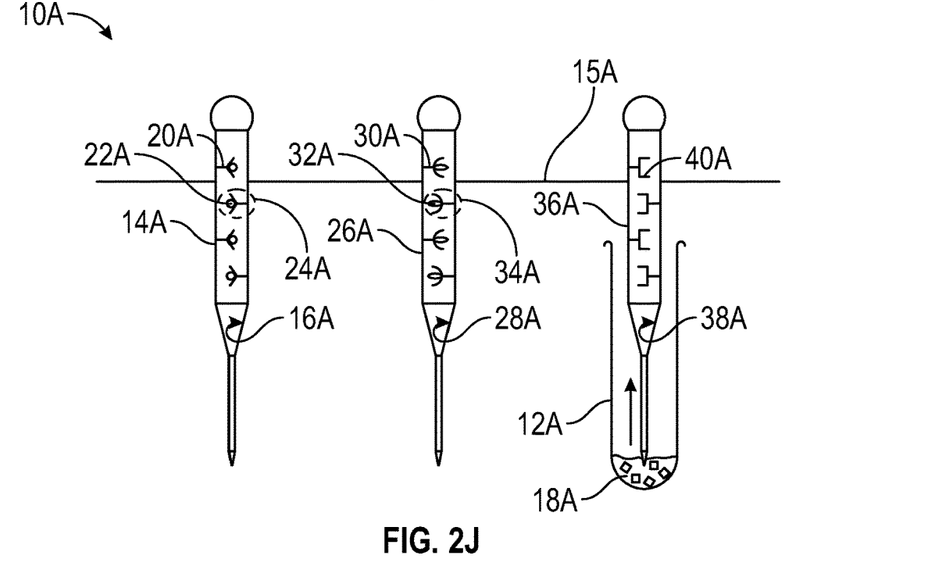
Figure 2K:
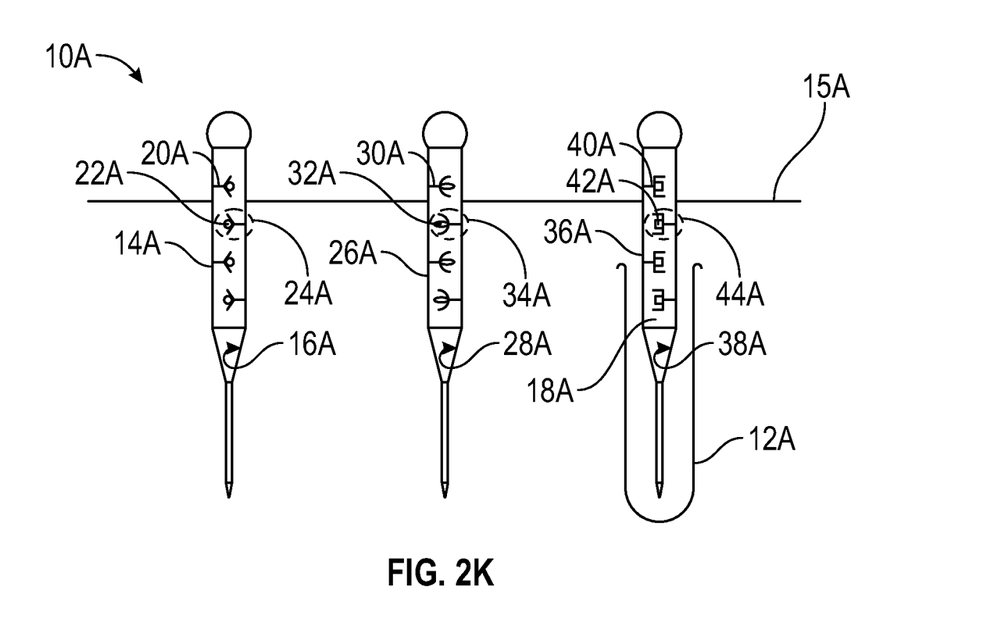
Figure 2L:
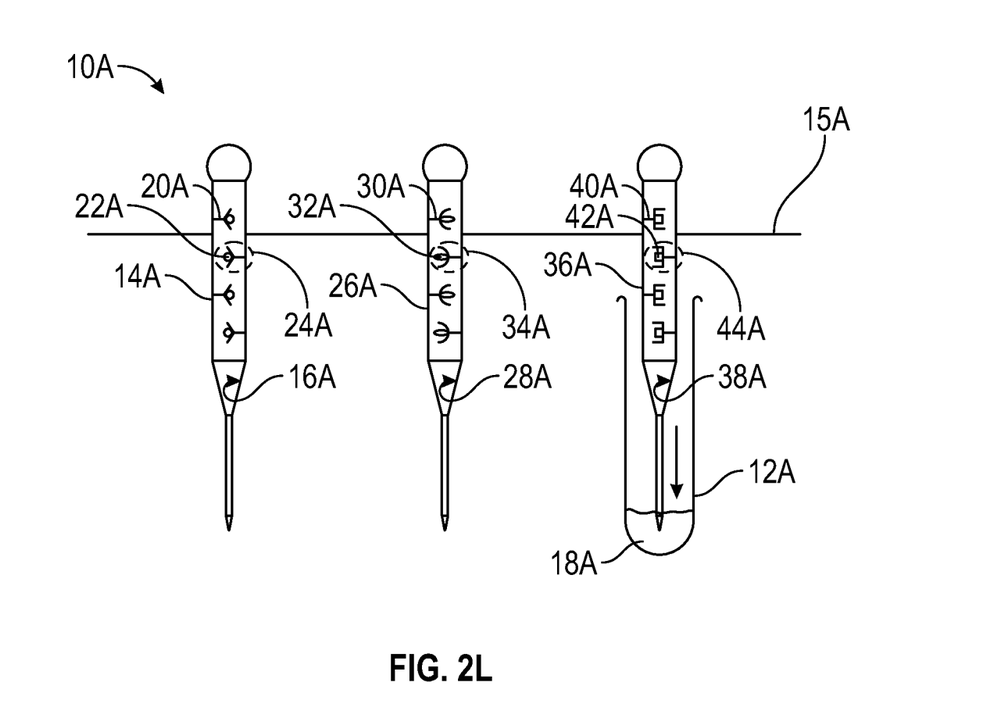

Referring now to FIGS. 21-2L, the third pipette 36A comprises an inner surface 38A on which a third immobilized capture antibody/binding partner 40A is present. The third immobilized capture antibody/binding partner 40A is different in analyte specificity from the first immobilized capture antibody/binding partner 20A and the second immobilized capture antibody/binding partner 30A, thereby allowing for association with and detection of a different and distinct analyte present in the single fluid sample 18A from the first analyte 22A and second analyte 32A present in the single fluid sample 18A. The third pipette 36A is disposed within sample receptacle 12A which contains the non-reacted portion of the single fluid sample 18A which has been re-dispensed into the sample receptacle 12A from the second pipette 26A. As shown in FIGS. 21-2L, with respect to the third pipette 36A, five third immobilized capture antibodies/binding partners 40A are shown as being immobilized on the inner surface 38A. However, one of ordinary skill in the art would recognize that any number of third immobilized capture antibodies/binding partners 40A may be immobilized on the inner surface 38A of the third pipette 36A. At least a portion of the non-reacted portion of the single fluid sample 18A is withdrawn into the third pipette 36A such that the single fluid sample 18A is in contact with the inner surface 38A of the third pipette 36A. As a result of this contact, the single fluid sample 18A comes into contact with the third immobilized capture antibody/binding partner 40A. If a third analyte of interest is present in the single fluid sample 18A, at least one third analyte-antibody complex 44A is formed by an association between the third analyte 42A present in the single fluid sample 18A and the third immobilized capture antibody/binding partner 40A present on the inner surface 38A of the third pipette 36A. A non-reacted portion of the single fluid sample 18A is re-dispensed into the sample receptacle 12A from the third pipette 36A. The third analyte 42A, if present, remains within the third pipette 36A (a reacted portion of the single fluid sample 18A) due to the association between the third analyte 42A and the third immobilized capture antibody/binding partner 40A forming the third analyte-antibody complex 44A present on the inner surface 38A of the third pipette 36A. Detection of the third analyte 42A within the third pipette 36A can be accomplished in accordance with any of the methodologies described herein or well known in the art. The detection can be either a qualitative or quantitative assessment of the presence of the third analyte 42A within the third pipette 36A and thereby indicative of the presence of the third analyte 42A in the single fluid sample 18A.

Non-Limiting Examples of the Inventive Concept(s)

A device for detecting the presence of at least two analytes in a fluid sample, the device comprising a pipetting station, wherein the pipetting station is configured to receive at least two pipettes, wherein the at least two pipettes comprises a first pipette having a first immobilized binding partner specific to a first analyte present on an inner surface of the first pipette and a second pipette having a second immobilized binding partner specific to a second analyte present on an inner surface of the second pipette, wherein the analyte specificity of the first immobilized binding partner is different than the analyte specificity of the second immobilized binding partner; wherein the first pipette is disposable within a fluid sample receptacle configured to hold a fluid sample, the first pipette configured to withdraw at least a portion of the single fluid sample into the first pipette such that the first immobilized binding partner is brought into contact with the withdrawn fluid sample to thereby form a first analyte-binding partner complex if a first analyte is present in the fluid sample; and further wherein a non-reacted portion of the single fluid sample is re-dispensable from the first pipette into the fluid sample receptacle, and thereafter the second pipette is disposable within the fluid sample receptacle whereby the second pipette is configured to withdraw at least a portion of the non-reacted portion of the fluid sample such that the second immobilized binding partner is brought into contact with the non-reacted portion of the withdrawn fluid sample to thereby form a second analyte-binding partner complex if a second analyte is present in the non-reacted portion of the single fluid sample.

The fluid sample of the device is selected from the group consisting of whole blood, blood plasma, blood serum, saliva, sputum, cerebrospinal fluid (CSF), intestinal fluid, intraperotineal fluid, cystic fluid, sweat, interstitial fluid, tears, mucus, urine, bladder wash, and semen.

The fluid sample of the device comprises a volume from about 1 microliter to about 100 microliters. The volume of the fluid sample of the device is about 50 microliters.

The sample receptacle of the device is selected from the group consisting of a well, cuvette, tube, vial, and capillary.

The first analyte and second analyte of the device are selected from the group consisting of cardiac markers, infectious disease serological analytes, therapeutic drugs, drugs of abuse, hormones, cancer markers, infectious disease nucleic acid analytes, autoimmune disease nucleic acid markers, proteins, vitamins, cofactors, metabolites, and combinations thereof.

The first immobilized binding partner and the second immobilized binding partner of the device are selected from the group consisting of intact monoclonal antibodies, polyclonal antibodies, multi-specific antibodies, bispecific antibodies, antibody fragments, receptors, ligands, aptamers, antigens, antibody substitute proteins or peptides, molecular imprinted polymers, and combinations thereof.

The first immobilized capture antibody and the second immobilized capture antibody of the device are selected from the group consisting of IgG, IgE, IgM, IgD, IgA, IgG1, IgG2, IgG3, IgG4, IgA1, IgA2, and combinations thereof.

A method for detecting the presence of at least two analytes in a fluid sample, the method comprising the steps of upon receipt of a fluid sample which may comprise an analyte, placing the single fluid sample in a sample receptacle; drawing the single fluid sample into a first pipette that is disposed within the sample receptacle, wherein a first immobilized binding partner is present on the an inner surface of the first pipette and the first immobilized binding partner is brought into contact with the fluid sample such that a first analyte-binding partner complex is formed if a first analyte is present in the single fluid sample; re-dispensing a non-reacted portion of the fluid sample from the first pipette and into the fluid sample receptacle; drawing the non-reacted portion of the fluid sample into a second pipette that is disposed within the sample receptacle, wherein a second immobilized binding partner having an analyte specificity different than the first immobilized binding partner is present on an inner surface of the second pipette and the second immobilized binding partner is brought into contact with the non-reacted portion of the fluid sample such that a second analyte-binding partner complex is formed if a second analyte is present in the non-reacted portion of the fluid sample; and detecting the presence of the first analyte-binding partner complex and the presence of the second analyte-binding partner complex.

The fluid sample of the method is selected from the group consisting of whole blood, blood plasma, blood serum, saliva, sputum, cerebrospinal fluid (CSF), intestinal fluid, intraperotineal fluid, cystic fluid, sweat, interstitial fluid, tears, mucus, urine, bladder wash, and semen.

The fluid sample of the method comprises a volume from about 1 microliter to about 100 microliters. The volume of the fluid sample of the device is about 50 microliters.

The sample receptacle of the method is selected from the group consisting of a well, cuvette, tube, vial, and capillary.

The first analyte and second analyte of the method are selected from the group consisting of cardiac markers, infectious disease serological analytes, therapeutic drugs, drugs of abuse, hormones, cancer markers, infectious disease nucleic acid analytes, autoimmune disease nucleic acid markers, proteins, vitamins, cofactors, metabolites, and combinations thereof.

The first immobilized binding partner and the second immobilized binding partner of the method are selected from the group consisting of intact monoclonal antibodies, polyclonal antibodies, multi-specific antibodies, bispecific antibodies, antibody fragments, receptors, ligands, aptamers, antigens, antibody substitute proteins and peptides, molecular imprinted polymers, and combinations thereof.

The first immobilized binding partner and the second immobilized binding partner of the method are selected from the group consisting of IgG, IgE, IgM, IgD, IgA, IgG1, IgG2, IgG3, IgG4, IgA1, IgA2, and combinations thereof.

The detection of the first analyte and the second analyte of the method is conducted via chemiluminescent detection, fluorescent detection, and combinations thereof.

A kit for detecting the presence of at least two analytes in a fluid sample, the kit comprising at least two pipettes, wherein the at least two pipettes comprises a first pipette having a first immobilized capture antibody specific to a first analyte present on an inner surface of the first pipette and a second pipette having a second immobilized capture antibody specific to a second analyte present on an inner surface of the second pipette, wherein the analyte specificity of the first immobilized capture antibody is different than the analyte specificity of the second immobilized capture antibody; a fluid sample receptacle, wherein the fluid sample receptacle is configured to hold a fluid sample; and providing instructions to a user to allow the user to use the kit to identify the presence of at least two analytes in the fluid sample.

Thus, in accordance with the presently disclosed and claimed inventive concept(s), there have been provided devices, methods, and kits that allow a small volume of a single fluid sample obtained from a patient to be re-used in order to detect at least two analytes present in such single fluid sample. Accordingly, a multiplexed panel associated with the various analytes present in the single fluid sample is created that fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. A method for detecting the presence of at least two analytes in a patient's single volume of fluid sample, the method comprising the steps of:
    placing the patient's single volume of fluid sample in a sample receptacle;
    drawing the single volume of fluid sample into a first pipette that is disposed within the sample receptacle, wherein a first immobilized binding partner specific to a first analyte is present on an inner surface of the first pipette and the first immobilized binding partner is brought into contact with the withdrawn single volume of fluid sample such that a first analyte-binding partner complex is formed if a first analyte is present in the single fluid sample;
    re-dispensing a non-reacted portion of the withdrawn single volume of fluid sample from the first pipette and into the fluid sample receptacle;
    drawing at least a portion of the re-dispensed single volume of fluid sample into a second pipette that is disposed within the sample receptacle, wherein a second immobilized binding partner specific to a second analyte is present on an inner surface of the second pipette, the second immobilized binding partner comprising an analyte specificity different from that of the first immobilized binding partner, further wherein the second immobilized binding partner is brought into contact with the re-dispensed single volume of fluid sample such that a second analyte-binding partner complex is formed if a second analyte is present in the re-dispensed fluid sample; and detecting the presence of the first analyte-binding partner complex and the presence of the second analyte-binding partner complex; and wherein the first and second pipettes are attached to a pipetting station that attaches the first and second pipettes to one another, whereby the pipetting station sequentially disposes the at least two pipettes within the fluid sample receptacle for performing the drawing and re-dispensing steps.

2. The method of claim 1, wherein the patient's single fluid sample is selected from the group consisting of whole blood, blood plasma, blood serum, saliva, sputum, cerebrospinal fluid (CSF), intestinal fluid, intraperitoneal fluid, cystic fluid, sweat, interstitial fluid, tears, mucus, urine, bladder wash, and semen.

3. The method of claim 1, wherein the patient's single fluid sample comprises a volume from about 1 microliter to about 100 microliters.

4. The method of claim 3, wherein the volume of the patient's single fluid sample is about 50 microliters.

5. The method of claim 1, wherein the first analyte and second analyte are selected from the group consisting of cardiac markers, infectious disease serological analytes, therapeutic drugs, drugs of abuse, hormones, cancer markers, infectious disease nucleic acid analytes, autoimmune disease nucleic acid markers, proteins, vitamins, cofactors, metabolites, and combinations thereof.

6. The method of claim 1, wherein the first immobilized binding partner and the second immobilized binding partner are selected from the group consisting of intact monoclonal antibodies, polyclonal antibodies, multi-specific antibodies, bispecific antibodies, antibody fragments, receptors, ligands, aptamers, antigens, antibody substitute proteins and peptides, molecular imprinted polymers, and combinations thereof.

7. The method of claim 6, wherein the first immobilized binding partner and the second immobilized binding partner are selected from the group consisting of IgG, IgE, IgM, IgD, IgA, IgG1, IgG2, IgG3, IgG4, IgA1, IgA2, and combinations thereof.

8. The method of claim 1, wherein the detection of the first analyte and the second analyte is conducted via chemiluminescent detection, fluorescent detection, and combinations thereof.

9. The method of claim 1, wherein the pipetting station sequentially disposes the at least two pipettes within the fluid sample receptacle via automated processes.

10. A method for detecting the presence of at least two analytes in a patient's single volume of fluid sample, the method comprising the steps of:

placing the patient's single volume of fluid sample in a sample receptacle, wherein the patient's single fluid sample comprises a volume from about 1 microliter to about 100 microliters;

drawing the single volume of fluid sample into a first pipette that is disposed within the sample receptacle, wherein a first immobilized binding partner specific to a first analyte is present on an inner surface of the first pipette and the first immobilized binding partner is brought into contact with the withdrawn single volume of fluid sample such that a first analyte-binding partner complex is formed if a first analyte is present in the single fluid sample;

re-dispensing a non-reacted portion of the withdrawn single volume of fluid sample from the first pipette and into the fluid sample receptacle;

drawing at least a portion of the re-dispensed single volume of fluid sample into a second pipette that is disposed within the sample receptacle, wherein a second immobilized binding partner specific to a second analyte is present on an inner surface of the second pipette, the second immobilized binding partner comprising an analyte specificity different from that of the first immobilized binding partner, further wherein the second immobilized binding partner is brought into contact with the re-dispensed single volume of fluid sample such that a second analyte-binding partner complex is formed if a second analyte is present in the re-dispensed fluid sample; and detecting the presence of the first analyte-binding partner complex and the presence of the second analyte-binding partner complex; and wherein the first and second pipettes are attached to a pipetting station that attaches the first and second pipettes to one another, whereby the pipetting station sequentially disposes the at least two pipettes within the fluid sample receptacle for performing the drawing and re-dispensing steps.

11. The method of claim 10, wherein the patient's single fluid sample is selected from the group consisting of whole blood, blood plasma, blood serum, saliva, sputum, cerebrospinal fluid (CSF), intestinal fluid, intraperitoneal fluid, cystic fluid, sweat, interstitial fluid, tears, mucus, urine, bladder wash, and semen.

12. The method of claim 10, wherein the first analyte and second analyte are selected from the group consisting of cardiac markers, infectious disease serological analytes, therapeutic drugs, drugs of abuse, hormones, cancer markers, infectious disease nucleic acid analytes, autoimmune disease nucleic acid markers, proteins, vitamins, cofactors, metabolites, and combinations thereof.

13. The method of claim 10, wherein the first immobilized binding partner and the second immobilized binding partner are selected from the group consisting of intact monoclonal antibodies, polyclonal antibodies, multi-specific antibodies, bispecific antibodies, antibody fragments, receptors, ligands, aptamers, antigens, antibody substitute proteins and peptides, molecular imprinted polymers, and combinations thereof.

14. The method of claim 10, wherein the detection of the first analyte and the second analyte is conducted via chemiluminescent detection, fluorescent detection, and combinations thereof.

15. The method of claim 10, wherein the pipetting station sequentially disposes the at least two pipettes within the fluid sample receptacle via automated processes.

16. A kit for detecting the presence of at least two analytes in a patient's single volume of fluid sample, the kit comprising:

at least two pipettes, wherein the at least two pipettes comprises a first pipette having a first immobilized capture antibody specific to a first analyte present on an inner surface of the first pipette and a second pipette having a second immobilized capture antibody specific to a second analyte present on an inner surface of the second pipette, wherein the analyte specificity of the first immobilized capture antibody is different than the analyte specificity of the second immobilized capture antibody;

a fluid sample receptacle, wherein the fluid sample receptacle is configured to hold a patient's single volume of fluid sample;

a pipetting station that attaches the at least two pipettes to one another, and wherein the pipetting station sequentially disposes the at least two pipettes within the fluid sample receptacle by an automated process in which the single volume of fluid sample is drawn from the fluid sample receptacle into the first pipette, re-dispensed back into the fluid sample receptacle, and then drawn from the fluid sample receptacle into the second pipette; and instructions to a user to allow the user to use the kit to identify the presence of at least two analytes in the single fluid sample.

17. The kit of claim 16, wherein the fluid sample receptacle is selected from the group consisting of a well, cuvette, tube, vial, and capillary.

18. The kit of claim 16, wherein the first analyte and second analyte are selected from the group consisting of cardiac markers, infectious disease serological analytes, therapeutic drugs, drugs of abuse, hormones, cancer markers, infectious disease nucleic acid analytes, autoimmune disease nucleic acid markers, proteins, vitamins, cofactors, metabolites, and combinations thereof.

19. The kit of claim 16, wherein the first immobilized binding partner and the second immobilized binding partner are selected from the group consisting of intact monoclonal antibodies, polyclonal antibodies, multi-specific antibodies, bispecific antibodies, antibody fragments, receptors, ligands, aptamers, antigens, antibody substitute proteins and peptides, molecular imprinted polymers, and combinations thereof.

20. The kit of claim 19, wherein the first immobilized binding partner and the second immobilized binding partner are selected from the group consisting of IgG, IgE, IgM, IgD, IgA, IgG1, IgG2, IgG3, IgG4, IgA1, IgA2, and combinations thereof.

* * * * *